United States Patent
Sun (10) Patent No.: US 6,780,648 B1
(45) Date of Patent: Aug. 24, 2004

(54) METHOD AND SYSTEM FOR SELECTIVELY DISTRIBUTING LUMINESCENCE MATERIAL PRECURSORS

(75) Inventor: Xiao-Dong Sun, Schenectady, NY (US)

(73) Assignee: General Electric Company, Schenectady, NY (US)

(*) Notice: Subject to any disclaimer, the term of this patent is extended or adjusted under 35 U.S.C. 154(b) by 239 days.

(21) Appl. No.: 09/666,382

(22) Filed: Sep. 20, 2000

(51) Int. Cl.$^7$ .......................... G01N 21/76; G01N 1/10; B01L 3/02

(52) U.S. Cl. .................. 436/172; 436/46; 436/171; 436/180; 422/65; 422/100; 73/863.32; 73/864.01; 73/864.11; 73/864.13; 73/864.17; 73/864.24; 73/864.25

(58) Field of Search .................. 436/46, 171–172, 436/180; 422/65, 100; 73/863.31, 863.32, 864.01, 864.11, 864.12, 864.13, 864.17, 864.18, 864.24, 864.25

(56) References Cited

U.S. PATENT DOCUMENTS

| | | | | |
|---|---|---|---|---|
| 3,568,735 A | * | 3/1971 | Lancaster | |
| 3,738,493 A | * | 6/1973 | Cummins et al. | 210/198 |
| 3,776,700 A | * | 12/1973 | Gallant | |
| 3,991,616 A | * | 11/1976 | Stahli | |
| 4,047,438 A | * | 9/1977 | Sekine | |
| 4,058,370 A | * | 11/1977 | Suovaniemi | |
| 4,106,911 A | * | 8/1978 | Marcelli | |
| 4,276,048 A | * | 6/1981 | Leaback | |
| 4,279,775 A | * | 7/1981 | Louderback et al. | 252/408 |
| 4,478,094 A | * | 10/1984 | Salomaa et al. | |
| 4,554,839 A | * | 11/1985 | Hewett et al. | |
| 4,622,032 A | * | 11/1986 | Katusra et al. | 604/122 |
| 4,798,095 A | * | 1/1989 | Itoh | |
| 4,879,109 A | * | 11/1989 | Hunter | 424/83 |
| 5,055,263 A | * | 10/1991 | Meltzer | |
| 5,143,854 A | | 9/1992 | Pirrung et al. | |
| 5,306,510 A | * | 4/1994 | Meltzer | |
| 5,336,468 A | * | 8/1994 | Tezuka et al. | 422/100 |
| 5,424,186 A | | 6/1995 | Fodor et al. | |
| 5,803,105 A | | 9/1998 | Wasson et al. | |
| 5,882,930 A | * | 3/1999 | Baier | |
| 5,959,297 A | | 9/1999 | Weinberg et al. | |
| 5,985,356 A | | 11/1999 | Schultz et al. | |
| 6,028,189 A | * | 2/2000 | Blanchard | |
| 6,034,775 A | | 3/2000 | McFarland et al. | |
| 6,045,671 A | | 4/2000 | Wu et al. | |
| 6,048,469 A | | 4/2000 | Xiang et al. | |

OTHER PUBLICATIONS

S. H. Cho et al, J. Electrochem. Soc. 1996, 143, L231–L234.*

(List continued on next page.)

Primary Examiner—Arlen Soderquist
(74) Attorney, Agent, or Firm—Andrew J. Caruso; Patrick K. Patnode (57) ABSTRACT

A method comprises positively displacing a first candidate luminescence material precursor from a dispenser to a first position of an array, displacing a second candidate luminescence material precursor from a dispenser mechanism to a second position of an array and simultaneously reacting the first and second candidates to produce a library of luminescence materials. A combinatorial high throughput screening liquid dispenser assembly comprises a battery of positive displacement driven dispensers for dispensing solutions of precursor luminescence materials, an array plate with wells to receive dispensed solution from the dispenser, a robotic positioning table supporting the array plate to position wells beneath respective dispensers and a controller to control dispensing of the solutions and positioning of the plate.

8 Claims, 5 Drawing Sheets

OTHER PUBLICATIONS

X.–D. Sun et al, Appl. Phys. Lett. 1997, 70, 3353–3355.*
X.–D. Sun et al, Appl. Phys. Lett. 1998, 72, 525–527.*
E. Danielson et al, Science 1998, 279, 837–839.*
J. Wang et al, Science 1998, 279, 1712–1714.*
E. D. Isaacs et al, Appl. Phys. Lett. 1998, 73, 1820–1822.*
E. W. McFarland et al, Trends in Biotechnology 1998, 17, 107–115.*
F. Wurthnere et al, Angew. Chem. Int. Ed. 1999, 38, 1649–1652.*
M. Kahl et al, Analytical Chemistry 1976, 48, 789–790.*
C. Stahli et al, Analytical Biochemistry 1978, 86, 1–20.*
J. Stanchfield et al, BioTechniques 1996, 20, 292–296.*
J. L. Wu et al, Materials Research Society Symposium Proceedings 1999, 560, 65–70.*
C. Jorgensen et al, SPIE 1999, 3857, 207–214.*
T. X. Sun et al, MRS Bulletin 2002, 27, 309–315.*
Prager, D. J. et al, Science 1965, 147, 606–608.*
Mellars, B. Chemical Abstracts 1977, 87, abstract 2023e.*
Martin, W. J. et al, Journal of Physics E: Scientific Instruments 1987, 20, 22–26.*
Szita, N. et al, SPIE 1998, 3258, 156–163.*
"A Combinatorial Approach to Materials Discovery", by Xiang et al., Science, 1995, vol. 268 (1995), pp. 1738–1740.
"A Class of Cobalt Oxide Magnetoresistance Materials Discovered with Combinatorial Synthesis", by Briceno et al., Science 270 (1995) pp. 273–275.
"A combinatorial approach to the discovery and optimization of luminescent materials", by Danielson et al., Nature 589 (1997) pp. 944–948.
"A Rare–Earth Phosphor Containing One–Dimensional Chains Identified Through Combinatorial Methods", by Danielson et al., Science 279 (1998) pp. 837–839.
"Combinatorial Searach for Advanced Luminescence Materials", by Sun, 61, 193201 (1999) pp. 193–201, Biotechnology & Bioengineering.

* cited by examiner fig. 1 fig. 2 fig. 3 fig. 4 fig. 5

METHOD AND SYSTEM FOR SELECTIVELY DISTRIBUTING LUMINESCENCE MATERIAL PRECURSORS

BACKGROUND OF THE INVENTION

The present invention relates to a method and system for selectively distributing reactant precursors to separate locations on a receiver. Particularly, the invention relates to a method and system for preparing a combinatorial library of luminescence material precursors for screening by combinatorial high throughput screening (CHTS).

Luminescence materials, also called phosphors, can convert a certain type of energy into electromagnetic radiation over thermal radiation. A phosphor is usually composed of a host lattice doped with fluorescent-active elements (activator) present in up to a few mole %. Phosphors have been widely used in fluorescent lamps, displays, scintillation, etc. Although the search for advanced phosphors started about a century ago, the new photonic technologies, including mercury-free fluorescent lamps, various flat panel displays, computed tomography (CT), etc., require new phosphors with advanced properties: These include high quantum efficiency, good absorption of the excitation energy, adequate color coordinate, long lifetime, and low cost.

The discovery of advanced oxide phosphors with multiple superior qualities for display applications remains a difficult problem. The specific spectral properties, absorption, quantum efficiencies, and lumen maintenance depend on complex interactions between the excitation source, host lattice, structural defects, and fluorescent dopants. Luminescence properties are highly sensitive to the changes in dopant composition, host stoichiometry, and processing conditions. Consequently, the identification of phosphors that are ideally suited to the requirements of a given display technology is highly empirical.

Combinatorial chemistry techniques have been applied to search for new phosphors in thin film form or powder form. Sun, Ted X., Biotechnology and Bioengineering Combinatorial Chemistry, 61, 4 (1998/1999) shows that a combination of a thin-film deposition and a masking strategy can be used to generate a thin film "spatially addressable library," where each sample precursor in the library is formed from a multiple-layer. Following deposition of precursor layers, interdiffusion of the layers can be effected by a thermal annealing step and the phosphors synthesized in a following high temperature step.

However, most phosphors used in industry are in powder form. The thin-film techniques result in libraries of materials that are substantially two-dimensional as opposed to a three dimensional powder form. The substantially two dimensional libraries cannot replicate the industrial powder form of phosphors and the results of testing the thin-film-created libraries can not always be extrapolated to industrial conditions.

In the synthesis of phosphor libraries in powder form, solutions of elemental precursors are dispensed using an automatic liquid injector with accurate control of volume. In this process, elemental precursors mix on a molecular scale prior to coprecipitation and high temperature synthesis. For example, in Xiang et al., U.S. Pat. No. 6,048,469, libraries of phosphor materials are generated using dispensers of a multi-jet delivery system. In this process, solutions of precursors are deposited by a "droplet-on-demand" ink jet system operated with a piezoelectric disc, which squeezes a drop of liquid when pulsed with an electric signal.

However, a multi-jet delivery system cannot handle viscose solutions or gels, gels or solid suspensions that are the necessary precursors of phosphor materials. Materials of a viscosity greater than about 1 centipoise tend to clog the orifices of multi-jet type systems. Some of the precursors are so viscous that they cannot be delivered through the ink-jet nozzle. Additionally, known multi-jet systems are designed for discovery processing of relatively benign materials. Many of the phosphor library precursors must be delivered as highly acidic solutions. The viscous solutions cannot be delivered through the orifices of the multi-jet type systems and the deleterious acidic phosphor solutions cause deterioration of known multi-jet delivery system structures.

There is a need for a method and apparatus to produce a precursor phosphor library that emulates forms of industrially used phosphors. Additionally, there is a need for a method and apparatus that will resist deteriorating effects of various phosphor precursor compositions.

BRIEF SUMMARY OF THE INVENTION

The invention meets these needs by providing a method and apparatus to deliver a library of precursor phosphor materials from solutions and gels of particle-sized materials and by providing a method and apparatus that resists the effects of deleterious precursor phosphor materials.

In a first embodiment, a method comprises positively displacing a first luminescence material precursor from a dispenser to a first position of an array, displacing a second luminescence material precursor from a dispenser mechanism to a second position of an array and simultaneously reacting the first and second precursors to produce a library of candidate luminescence materials.

In another embodiment, the invention relates to a method, comprising establishing a combinatorial library of precursor luminescence materials, effecting parallel reaction of said library to produce a library of candidate luminescence materials and evaluating each candidate material to select a best material from among said candidate library.

In another embodiment, the invention relates to a combinatorial high throughput screening liquid dispenser assembly. The assembly comprises a battery of positive displacement driven dispensers for dispensing solutions of precursor luminescence materials, an array plate with wells to receive dispensed solution from the dispenser, a robotic positioning table supporting the array plate to position wells beneath respective dispensers and a controller to control dispensing of the solutions and positioning of the plate.

In still another embodiment, the invention relates to a combinatorial high throughput screening system. The system includes the dispensing assembly, a furnace to heat treat solutions of precursor luminescence materials in the wells and an evaluator to evaluate luminescence materials from the precursors.

DETAILED DESCRIPTION OF THE INVENTION

The invention relates to a combinatorial chemistry approach to screening and selecting luminescence materials.

In a first aspect, the invention relates to a method and apparatus for producing a library of luminescence materials for combinatorial high throughput screening (CHTS).

These and other features will become apparent from the drawings and following detailed discussion, which by way of example without limitation describe preferred embodiments of the present invention.

Figure 1:
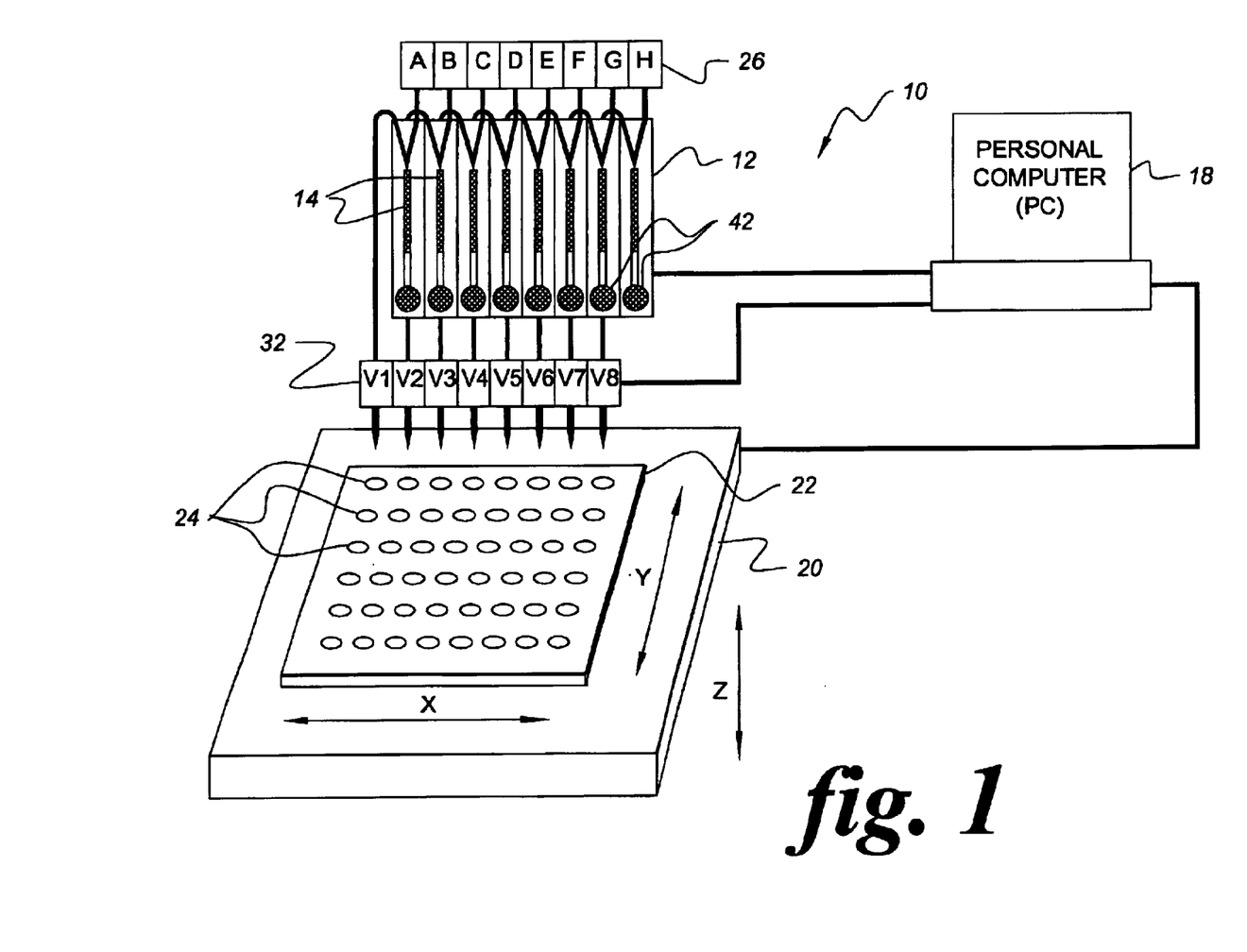
FIG. 1 is a schematic representation of a combinatorial high throughput screening liquid dispenser assembly.
Figure 2:
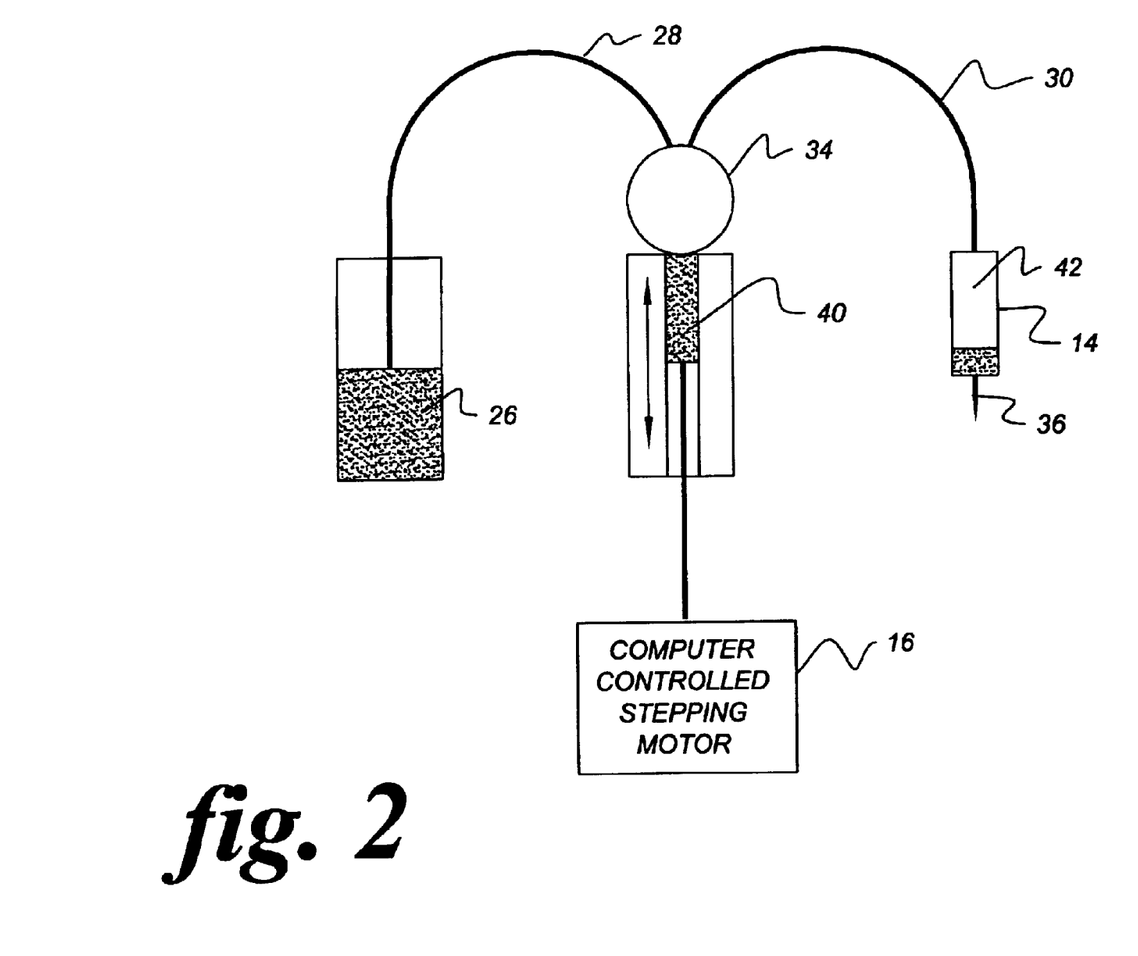
FIG. 2 is a schematic representation a positive displacement device of the assembly of FIG. 1.

FIG. 1 schematic represents a combinatorial high throughput screening liquid dispensing assembly with an array of 8 positive displacement syringes and FIG. 2 schematically represents a positive displacement device of the assembly 10 of FIG. 1. In FIG. 1, assembly 10 includes a battery 12 of positive displacement syringes 14 that are driven by stepping motor 16 (shown in FIG. 2), which in turn is controlled by computer 18. The dispensing assembly 10 further includes X-Y-Z robotic positioning stage 20, which supports array plate 22. X-Y-Z robotic positioning stage 20 is controlled by computer 18 to position wells 24 of the array plate 22 beneath respective positive displacement syringes 14 for delivery of test solutions from reservoirs 26.

Referring to FIGS. 1 and 2, each syringe 14 is a positive displacement device with a connecting line 28 to a chemical reservoir 26, a connecting line 30 to syringe 14 and three-way valve 34. Syringe 14 includes microsolenoid valve 34 and removable tip 36. Three way fluid valve 34 is driven by stepping motor 16, which is controlled by computer 18. In operation, computer 18 controls stepping motor 16 to open valve 34 to reservoir connecting line 28 and to withdraw valve plunger 40 toward the motor to aspirate a solution of luminescence material precursor into chamber 42. Valve 34 then closes connecting line 28 and opens connecting line 30 to syringe 14. The computer 18 causes stepping motor 16 to drive plunger 40 to mechanically displace precursor solution from chamber 42 to syringe 14 through solenoid valve 32. Solenoid valve 32 is closed until plunger 40 is driven to displace material. The additional liquid control of the solenoid valve allows for a non-contact dispensing of a fluid drop to a respective well 24 of plate 22.

Computer 18 controls aspiration of precursor solution into the battery 12 of syringes 14 and sequential positioning of the wells 24 of array place 22 so that a prescribed stoichiometry and/or composition of luminescence precursor can be delivered to the wells 24. By coordinating activation of the syringes 14 and movement of plate 22 on the robotic X-Y-Z, a library of the luminescence precursor materials can be generated in a two-dimensional array for use in a combinatorial high throughput screening method.

The method and system of the invention can advantageously accommodate solutions and gels having a viscosity greater than about 1 centipoise to about 100 centipoise. Additionally, the method and system can dispense highly viscose solid in fluid suspensions of up to about 100 centipoise and particle size of up to about 50 $\mu$m.

A dispenser assembly 10 can be fabricated by providing a battery of eight automated nano-liter liquid syringes 14 as shown in FIG. 1. Each syringe 14 is individually controlled and programmed with a dual function of aspiration and dispensing, with a linear dynamic range (deliverable volume range per drop) of from about 4 nano-liter to about 250 micro-liter. The dynamic range can be from about 20 nano-liter to about 100 micro-liter, preferably from about 100 nano-liter to about 50 micro-liter. A matching array plate 22 of reaction wells 24 can be machined from alumina or quartz. The plate 22 is placed in registry with the syringe battery 12 so that syringe tip to tip separation matches well to well separation. By coordinating the movement of the syringe battery 12 and by changing amount of solution delivered, a 128-membered solution precursors of a phosphor materials library can be generated in about 10 minutes.

Figure 3:
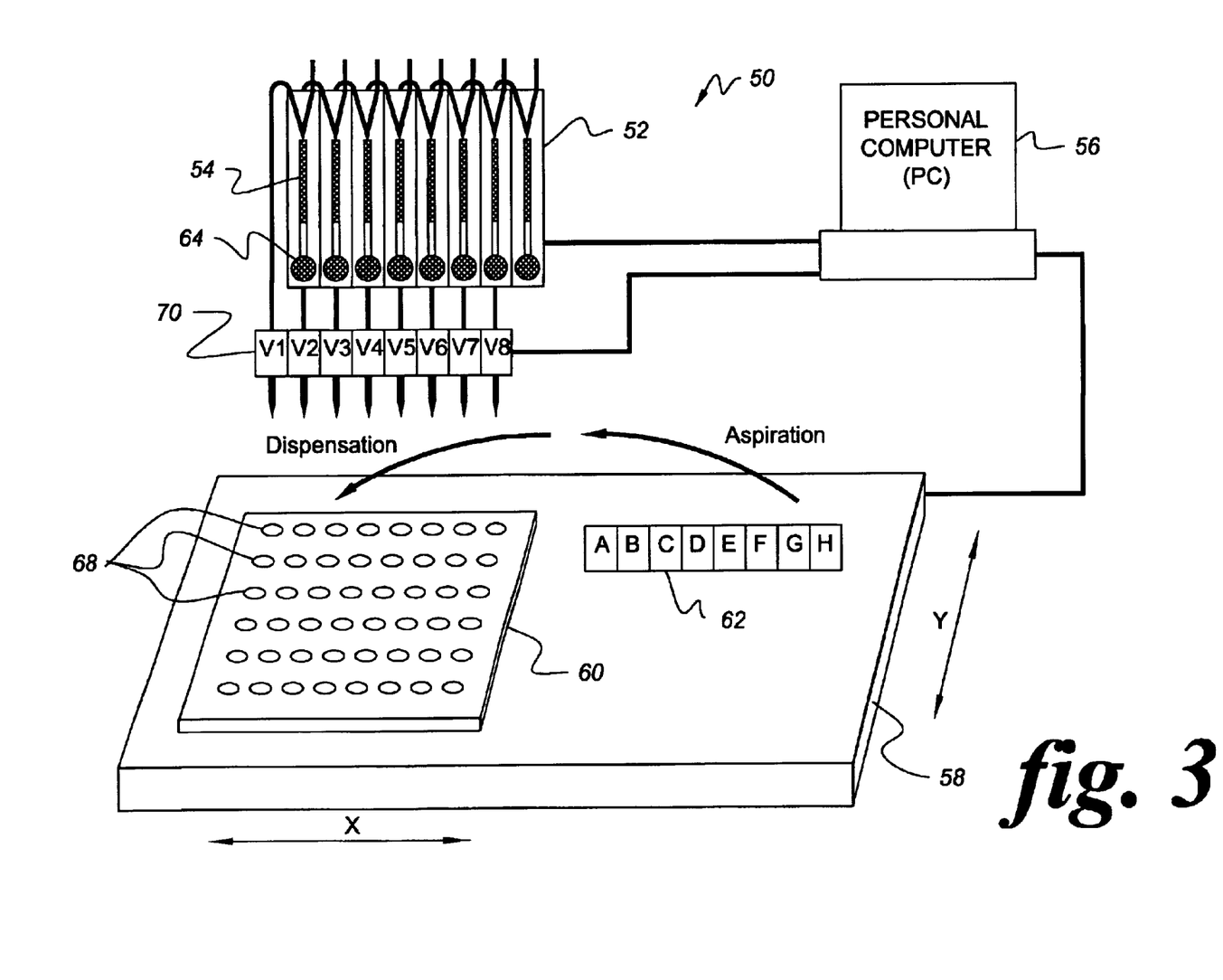
FIG. 3 is a schematic representation of another combinatorial high throughput screening liquid dispenser assembly.

FIG. 3 is a schematic representation of another dispensing assembly 50 of the invention. Assembly 50 includes a battery 52 of positive displacement syringes 54 that are driven by a step motor, controlled by computer 56 in a similar fashion as shown in FIG. 2. In this embodiment however, solution precursors are aspirated through dispenser tips 36 and then moved to corresponding well-positions of the array plate 22 and dispensed volumetrically. This is unlike the scheme shown in FIGS. 1 and 2, where solution precursors are fed into dispenser tips 36 through the three way valve 34. In FIG. 3, syringe battery 52 is robotically controlled by a computer 56 driven motor for displacement up and down in a Z-axis direction. The dispensing assembly 50 further includes X-Y robotic positioning stage 58, which supports both an array plate 60 and reservoirs 62 containing luminescence precursor material solutions. X-Y robotic positioning stage 58 is controlled by computer 56 to position reservoirs 62 beneath respective positive displacement syringes 54. The battery 52 of syringes 54 is then activated in a vertical Z direction into contact with respective reservoirs 62. Solution is aspirated into respective chambers 64 of syringes 54 by operation of the stepping motor and valve arrangement of FIG. 2. Computer 56 then controls the robotic mechanism to displace the syringe battery 52 upwardly. X-Y robotic positioning stage 58 controlled by computer 56, positions wells 68 of plate 60 beneath respective syringes 54 and lowers the syringes toward the wells 68 to a position for delivery of solution. The computer 56 then activates solenoid valves 72 and the stepping motor to mechanically displace a volume of precursor solution from each chamber 64 of each syringe 54 through solenoid valve 72 to deliver solution to a respective well 68 of plate 60. Each aspirated volume can be controlled by computer 56 so that different volumes or different proportions can be delivered to separate respective wells. The dispenser of FIG. 3 can be used to handle highly viscous and/or corrosive materials. The dispenser of FIG. 3 can easily handle solid/liquid suspensions and emulsions.

The assembly of the invention generates a library of luminescence precursor solutions in a two-dimensional array for use in a combinatorial high throughput screening method (CHTS). Typically, a CHTS is characterized by parallel reactions at a micro scale. In the invention, the CHTS can be described as comprising (A) (i) aspirating a candidate luminescence material precursor into a hollow tube by action of a plunger; (ii) dispensing the precursor into a well of an array plate by a positive displacement action of a plunger against the precursor; (iii) effecting a reaction of the precursor to form a candidate luminescence material; and (iv) evaluating the candidate luminescence material. The method includes (B) reiterating (A) wherein a successive candidate luminescence material precursor for a step (i) is selected as a result of an evaluating step (iii) of a preceding iteration of (A).

Figure 4:
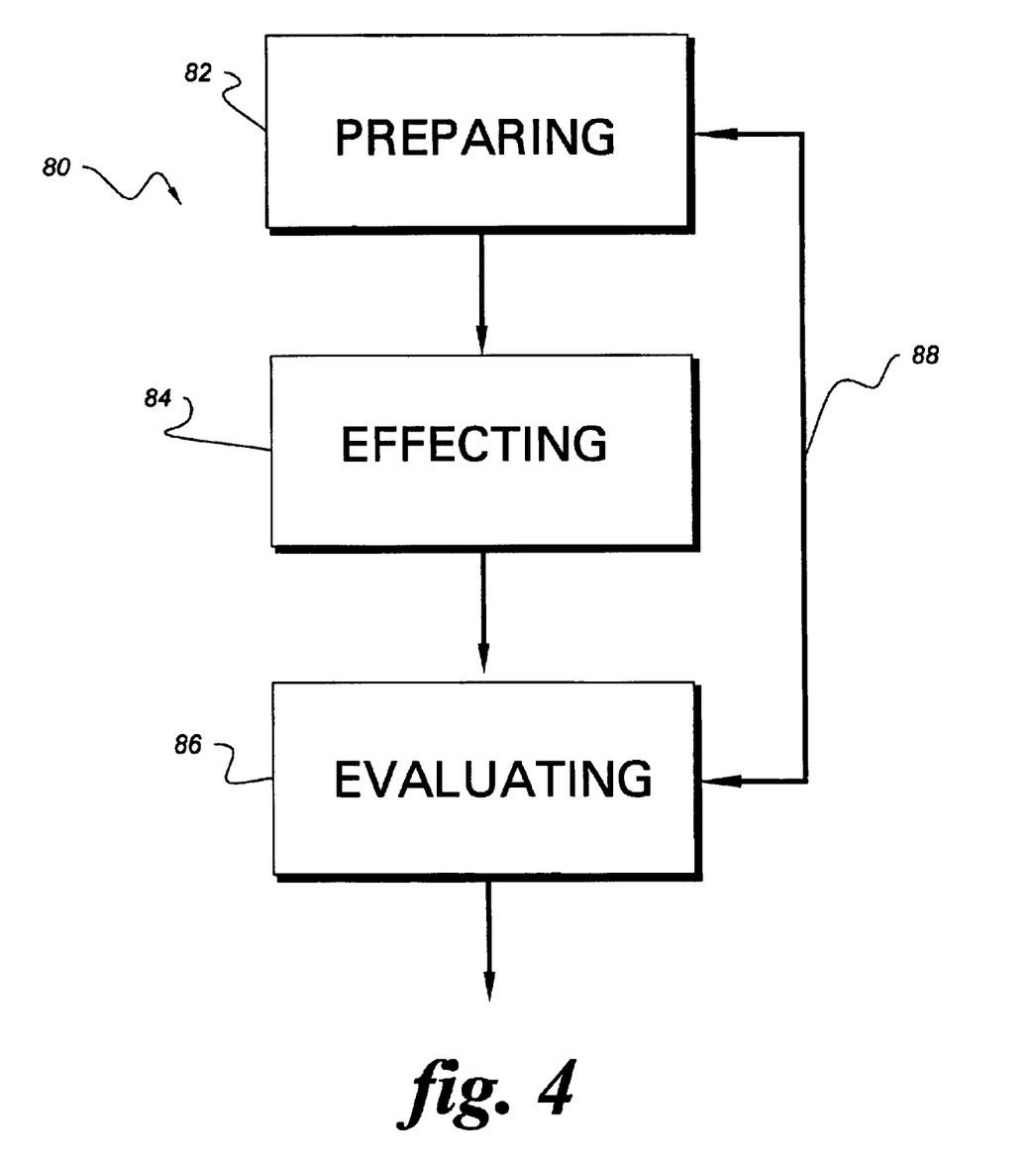
FIG. 4 is a flow chart of a method for screening luminescence materials.

FIG. 4 shows an overall CHTS method, including preparation of a phosphor precursor library to conversion to final phosphor library by a thermal process and evaluation with fluorescent screening. The screening result narrows down a space of search for design and preparation of a next phosphor library. The method 80 includes delivering 82 candidates of luminescence material precursors by positively displacing the precursors to produce a library of precursors. The precursors are dried, calcined and annealed 84. In these procedures, the library is first placed on an orbital shaker and precursors in each well are thoroughly mixed. The library is then baked at about 80° C. in an oven to dry fluid. The library is then calcined at about 300° C. to about 700° C. to convert precursors to oxide phosphors. Finally, the library is sintered at about 800° C. to about 1500° C. to form luminescence materials. The luminescence materials are then evaluated 86. Color photography of the luminescence material library can provide comparison of the brightness and chromaticity of the materials. A high throughput CCD (charge coupling device) based spectrometer can also be used to image the fluorescence of the library. This instrument is preferred since it permits a high throughput synthesis and screening of fluorescence materials up to a daily screening rate of 100 to 1,000. The evaluating step can be used to identify candidate precursor materials for further screening. In this embodiment, the steps of delivering the precursors, drying, calcining and annealing and evaluating the precursors are reiterated 88 to identify "best" luminescence materials or to identify next candidate precursor materials for a next iteration.

In one aspect, the CHTS can be described with reference to FIG. 4 as a method 80 comprising (A) (i) preparing 82 a library of luminescence precursor materials by dispensing a solution of the precursor into a well of an array plate by a positive displacement action; (ii) effecting 84 a reaction of the precursor to form a candidate luminescence material; and (iii) evaluating 86 the candidate luminescence material. The method includes (B) reiterating 88 (A) wherein a successive candidate luminescence material precursor for a step (i) is selected as a result of an evaluating step (iii) of a preceding iteration of (A).

The following Example describes a preferred embodiment of the invention.

EXAMPLE

A powder phosphor library: $(Y_xA_{1-x})_3(Al_yGa_{1-y})_5O_{12}:Ce^{3+}$ (A: Gd, Lu) was prepared as follows. A sintered alumina (99.5% purity) plate with 128 (8 by 16 array) cells of 2 mm in diameter and ~6 mm in depth was machined and used as a containing plate for liquid precursors to powder phosphors. Neighboring cells were 3 mm in center to center separation and registered in position to the array of liquid dispenser. By coordinating the scanning motion of a X-Y-Z table mounted with the substrate plate in the spatial resolution of 0.1 mm, and variation of liquid volumes from dispenser, a library with 128 different solution mixing precursors of powder phosphors was generated in a matter of minutes. First, a continuously decreasing volume of $Y(NO_3)_3$ was dispensed by positive displacement into each array well in the X-direction. A continuously increasing volume of $A(NO_3)_3$ was then delivered in the same direction. The total volume of $Y(NO_3)_3$ and $A(NO_3)_3$ in each well was 3 mmol. A corresponding gradient of $Al(NO_3)_3$ and $Ga(NO_3)_3$ was delivered in the Y-direction of the array to provide a total of 5 mmol. in each well. Finally a uniform amount of $Ce(NO_3)_3$ was delivered to each well.

High purity ($\geq 99.9\%$) clear aqueous nitrate solutions were used in making the powder library: $Y(NO_3)_3$, (1M), $Gd(NO_3)_3$ (1M), $Lu(NO_3)_3$ (1M), $Al(NO_3)_3$ (1M), $Ga(NO_3)_3$ (1M), $Ce(NO_3)_3$ (0.5M). A phosphor precursor solution library was generated on the alumina plate (with 128 sample cells) according to the described scheme of X-Y delivery. The total amount of samples in each cell was approximately 10 $\mu$mole. The composition of each cell is listed in TABLE 1, within the general formula $(Y_xA_{1-x})_3(Al_yGa_{1-y})_5O_{12}:Ce^{3+}_{0.06}$(A: Gd, Lu), where $3 \geq x \geq 0.375$; $5 \geq y \geq 0.625$. The library was placed on an orbital shaker for mixing while over shining with an IR lamp to evaporate the solvent, with surface temperature approximately 800° C. After samples are dried, the library was placed in a reducing furnace at 1400° C. for 2 hours with heating and cooling controlled at ~10° C./minute.

TABLE 1

| | |
|---|---|
| Lu2.625Y0.376Al5Ce0.06 | Lu2.25Y0.75Al5Ce0.06 |
| Lu2.625Y0.375Al4.375Ga0.625Ce0.0 | Lu2.25Y0.75Al4.375Ga0.625Ce0.06 |
| Lu2.625Y0.375Al3.75Ga1.25Ce0.06 | Lu2.25Y0.75Al3.75Ga1.25Ce0.06 |
| Lu2.625Y0.375Al3.125Ga1.25C30.0 | Lu2.25Y0.75Al3.125Ga1.875Ce0.06 |
| Lu2.625Y0.375Al2.5Ga2.5Ce0.06 | Lu2.25Y0.75Al2.5Ga2.5Ce0.06 |
| Lu2.625Y0.375Al1.875Ga3.125Ce0.0 | Lu2.25Y0.75Al1.875Ga3.125Ce0.06 |
| Lu2.625Y0.375Al1.25Ga3.75Ce0.06 | Lu2.25Y0.75Al1.25Ga3.75Ce0.06 |
| Lu2.625Y0.375Al0.625Ga4.375Ce0.0 | Lu2.25Y0.75Al0.625Ga4.375Ce0.06 |
| Gd2.625Y0.375Al5Ce0.06 | Gd2.25Y0.75Al5Ce0.06 |
| Gd2.625Y0.375Al4.375Ga0.625Ce0.0 | Gd2.25Y0.75Al4.375Ga0.625Ce0.06 |
| Gd2.625Y0.375Al3.75Ga1.25Ce0.06 | Gd2.25Y0.75Al3.75Ga1.25Ce0.06 |
| Gd2.625Y0.375Al3.125Ga1.875Ce0.0 | Gd2.25Y0.75Al3.125Ga1.875Ce0.06 |
| Gd2.625Y0.375Al2.Ga2.5Ce0.06 | Gd2.25Y0.75Al2.5Ga2.5Ce0.06 |
| Gd2.625Y0.375Al1.875Ga3.125Ce0.0 | Gd2.25Y0.75Al1.875Ga3.125Ce0.06 |
| Gd2.625Y0.375Al1.25Ga3.75Ce0.06 | Gd2.25Y0.75Al1.25Ga3.75Ce0.06 |
| Gd2.625Y0.375Al0.625Ga4.375Ce0.0 | Gd2.25Y0.75Al0.625Ga4.375Ce0.06 |
| Lu1.125Y1.875Al5Ce0.06 | Lu0.75Y2.25Al5Ce0.06 |
| Lu1.125Y1.875Al4.375Ga0.625Ce0.06 | Lu0.75Y2.25Al4.375Ga0.625Ce0.06 |
| Lu1.125Y1.875Al3.75Ga1.25Ce0.06 | Lu0.75Y2.25Al3.75Ga1.25Ce0.06 |
| Lu1.125Y1.875Al3.12Ga1.875Ce0.06 | Lu0.75Y2.25Al3.125Ga1.875Ce0.06 |
| Lu1.125Y1.875Al2.5Ga2.5Ce0.06 | Lu0.75Y2.25Al2.5Ga2.5Ce0.06 |
| Lu1.125Y1.875Al1.875Ga3.125Ce0.06 | Lu0.75Y2.25Al1.875Ga3.125Ce0.06 |
| Lu1.125Y1.875Al1.25Ga3.75Ce0.06 | Lu0.75Y2.25Al1.25Ga3.75Ce0.06 |
| Lu1.125Y1.875Al0.625Ga4.375Ce0.06 | Lu0.75Y2.25Al0.625Ga4.375Ce0.06 |
| Gd1.125Y1.875Al5Ce0.06 | Gd0.75Y2.25Al5Ce0.06 |
| Gd1.125Y1.875Al4.375Ga0.625Ce0.06 | Gd0.75Y2.25Al4.375Ga0.625Ce0.0 |
| Gd1.125Y1.875Al3.75Ga1.25Ce0.06 | Gd0.75Y2.25Al3.75Ga1.25Ce0.06 |
| Gd1.125Y1.875Al3.125Ga1.875Ce0.06 | Gd0.75Y2.25Al3.125Ga1.875Ce0.0 |
| Gd1.125Y1.875Al2.5Ga2.5Ce0.06 | Gd0.75Y2.25Al2.5Ga2.5Ce0.06 |
| Gd1.125Y1.875Al1.875Ga3.125Ce0.06 | Gd0.75Y2.25Al1.875Ga3.125Ce0.0 |
| Gd1.125Y1.875Al1.25Ga3.75Ce0.06 | Gd0.75Y2.25Al1.25Ga3.75Ce0.06 |
| Gd1.125Y1.875Al0.625Ga4.375Ce0.06 | Gd0.75Y2.25Al0.625Ga4.375Ce0.0 |

TABLE 1-continued

| | |
|---|---|
| Lu1.875Y1.125Al5Ce0.06 | Lu1.5Y1.5Al5Ce0.06 |
| Lu1.875Y1.125Al4.375Ga0.625Ce0.06 | Lu1.5Y1.5Al4.375Ga0.625Ce0.06 |
| Lu1.875Y1.125Al3.75Ga1.25Ce0.06 | Lu1.5Y1.5Al3.75Ga1.25Ce0.06 |
| Lu1.875Y1.125Al3.125Ga1.875Ce0.06 | Lu1.5Y1.5Al3.125Ga1.875Ce0.06 |
| Lu1.875Y1.125Al2.5Ga2.5Ce0.06 | Lu1.5Y1.5Al2.5Ga2.5Ce0.06 |
| Lu1.875Y1.125Al1.875Ga3.125Ce0.06 | Lu1.5Y1.5Al1.875Ga3.125Ce0.06 |
| Lu1.875Y1.125Al1.25Ga3.75Ce0.06 | Lu1.5Y1.5Al1.25Ga3.75Ce0.06 |
| Lu1.875Y1.125Al0.625Ga4.375Ce0.06 | Lu1.5Y1.5Al0.625Ga4.375Ce0.06 |
| Gd1.875Y1.125Al5Ce0.06 | Gd1.5Y1.5Al5Ce0.06 |
| Gd1.875Y1.125Al4.375Ga0.625Ce0.06 | Gd1.5Y1.5Al4.375Ga0.625Ce0.06 |
| Gd1.875Y1.125Al3.75Ga1.25Ce0.06 | Gd1.5Y1.5Al3.75Ga1.25Ce0.06 |
| Gd1.875Y1.125Al3.125Ga1.875Ce0.06 | Gd1.5Y1.5Al3.125Ga1.875Ce0.06 |
| Gd1.875Y1.125Al2.5Ga2.5Ce0.06 | Gd1.5Y1.5Al2.5Ga2.5Ce0.06 |
| Gd1.875Y1.125Al1.875Ga3.125Ce0.06 | Gd1.5Y1.5Al1.875Ga3.125Ce0.06 |
| Gd1.875Y1.125Al1.25Ga3.75Ce0.06 | Gd1.5Y1.5Al1.25Ga3.75Ce0.06 |
| Gd1.875Y1.125Al0.625Ga4.375Ce0.06 | Gd1.5Y1.5Al0.625Ga4.375Ce0.06 |
| Lu0.375Y2.625Al5Ce0.06 | Y3Al5Ce0.06 |
| Lu0.375Y2.625Al4.375Ga0.625Ce0.06 | Y3Al4.375Ga0.625Ce0.06 |
| Lu0.375Y2.625Al3.75Ga1.25Ce0.06 | Y3Al3.75Ga1.25Ce0.06 |
| Lu0.375Y2.625Al3.125Ga1.875Ce0.06 | Y3Al3.125Ga1.875Ce0.06 |
| Lu0.375Y2.625Al2.5Ga2.5Ce0.06 | Y3Al2.6Ga2.5Ce0.06 |
| Lu0.375Y2.625Al1.875Ga3.125Ce0.06 | Y3Al1.875Ga3.125Ce0.06 |
| Lu0.375Y2.625Al1.25Ga3.75Ce0.06 | Y3Al1.25Ga3.75Ce0.06 |
| Lu0.375Y2.625Al0.625Ga4.375Ce0.06 | Y3Al0.625Ga4.375Ce0.06 |
| Gd0.375Y2.625Al5Ce0.06 | Y3Al5Ce0.06 |
| Gd0.375Y2.625Al4.375Ga0.625Ce0.0 | Y3Al4.375Ga0.625Ce0.06 |
| Gd0.375Y2.625Al3.75Ga1.25Ce0.06 | Y3Al3.75Ga1.25Ce0.06 |
| Gd0.375Y2.625Al3.125Ga1.875Ce0.0 | Y3Al3.125Ga1.875Ce0.06 |
| Gd0.375Y2.625Al2.5Ga2.5Ce0.06 | Y3Al2.5Ga2.5Ce0.06 |
| Gd0.375Y2.625Al1.875Ga3.125Ce0.0 | Y3Al1.875Ga3.125Ce0.06 |
| Gd0.375Y2.625Al1.25Ga3.75Ce0.06 | Y3Al1.25Ga3.75Ce0.06 |
| Gd0.375Y2.625Al0.625Ga4.375Ce0.0 | Y3Al0.625Ga4.375Ce0.06 |

Figure 5:
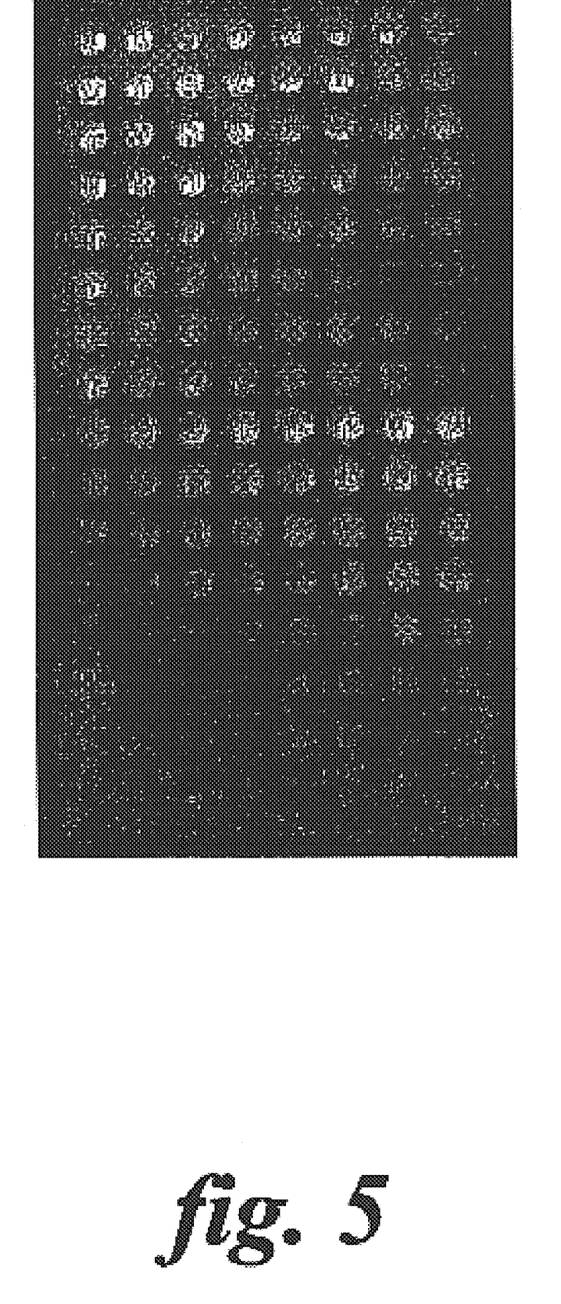
FIG. 5 is a fluorescent intensity image phosphor library.

After thermal treatment, there is no detectable cross contamination of neighboring samples and no apparent alumina substrate effect on the phosphor library. The as synthesized powder phosphor library was placed under a uniform long UV (370 nm) excitation. The fluorescent image of the library is shown in FIG. 5. FIG. 5 shows an array of different phosphors synthesized simultaneously in accordance with the invention. The phosphor library of FIG. 5 corresponds to the composition map shown in TABLE 1. Fluorescence of each phosphor corresponds to location brightness of respective phosphors of the library as shown. Three distinguishable emitting colors, orange-yellow-green, were obtained from this series of phosphors, by elemental substitution.

Qualitative composition/property relationships can be determined from the library. For example, the following relationships were determined:

1. Increase of Ga3+ in (YxCe0.06Lu1-x)3(AlyGa1-y)5O12 decreases emission wavelength and emission intensity.

2. Increase of Lu3+ in (YxCe0.06Lu1-x)3(AlyGa1-y)5O12 slightly increases emission intensity and slightly decreases emission wavelength, W.

3. Increase of Gd3+ for lesser Ga3+ (YxCe0.06Lu1-x)3 (AlyGa1-y)5O12 causes a red shift of emission wavelength, for higher Ga3+, increase of Gd3+ quenches emission intensity.

These studies permit optimization of emitting intensity of phosphors for each desired color from this series of compositions.

While preferred embodiments of the invention have been described, the present invention is capable of variation and modification and therefore should not be limited to the precise details of the Examples. The invention includes changes and alterations that fall within the purview of the following claims.

What is claimed is:

1. A method to investigate properties of luminescence materials, comprising:

mechanically positively displacing first luminescence material precursors selected from the group consisting of $Y(NO_3)_3$, $Gd(NO_3)_3$, $Lu(NO_3)_3$, $Al(NO_3)_3$, $Ga(NO_3)_3$ and $Ce(NO_3)_3$ with a plunger from a dispenser to a first position of a combinatorial array plate, and mechanically positively displacing further luminescence material precursors wherein at least one of the first luminescence material precursors is displaced within a linear dynamic range of from greater than 20 nano-liter to about 100 micro-liter; and simultaneously reacting the luminescence material precursors to produce a first $(Y_xA_{1-x})_3(Al_yGa_{1-y})_5O_{12}$: $Ce^{3+}_{0.06}$(A: Gd, Lu), where $3 \geq x \geq 0.375$; $5 \geq y \geq 0.625$, library of candidate luminescence materials;

determining wavelength and emission intensity of fluorescence of the first $(Y_xA_{1-x})_3(Al_yGa_{1-y})_5O_{12}$:$Ce^{3+}_{0.06}$ (A: Gd, Lu) library of materials under an applied UV excitation; and defining a next $(Y_xA_{1-x})_3(Al_yGa_{1-y})_5O_{12}$:$Ce^{3+}_{0.06}$(A: Gd, Lu) library of candidate luminescence materials according to the determined wavelength and emission intensity of the first $(Y_xA_{1-x})_3(Al_yGa_{1-y})_5O_{12}$:$Ce^{3+}_{0.06}$ (A: Gd, Lu) library of materials.

2. The method of claim 1, comprising displacing said precursors from respective hollow barrels by activating a plunger within each of said barrels.

3. The method of claim 1, wherein said at least one of the first precursors is displaced within a linear dynamic range of from about 100 nano-liter to about 50 micro-liter.

4. The method of claim 1, comprising first aspirating said first luminescence material precursors into said dispenser.

5. The method of claim 4, wherein said first luminescence material precursors are aspirated into said dispenser within a linear dynamic range of from about 100 nano-liter to about 50 micro-liter.

6. The method of claim 1, wherein said precursors are highly viscous materials.

7. The method of claim 1, wherein said precursors have a viscosity of greater than about 1 centipoise to about 100 centipoise.

8. The method of claim 1, wherein said precursors comprise a solid in fluid suspension of a particle size of up to about 50 $\mu$m.

* * * * *